(12) United States Patent
Brummel et al.

(10) Patent No.: US 8,050,944 B2
(45) Date of Patent: Nov. 1, 2011

(54) INTELLIGENT PATIENT VISIT INFORMATION MANAGEMENT AND NAVIGATION SYSTEM

(75) Inventors: Tony Brummel, Middleton, WI (US); Christopher Alban, Madison, WI (US); Brad Eichhorst, Verona, WI (US); Aaron T. Cornelius, Mount Horeb, WI (US)

(73) Assignee: Epic Systems Corporation, Verona, WI (US)

( * ) Notice: Subject to any disclaimer, the term of this patent is extended or adjusted under 35 U.S.C. 154(b) by 1757 days.

(21) Appl. No.: 09/950,242

(22) Filed: Sep. 10, 2001

(65) Prior Publication Data

US 2002/0035487 A1 Mar. 21, 2002

Related U.S. Application Data

(60) Provisional application No. 60/233,949, filed on Sep. 20, 2000.

(51) Int. Cl.
*G06Q 10/00* (2006.01)
(52) U.S. Cl. ............................................. 705/3; 705/2
(58) Field of Classification Search ................... 705/2–3
See application file for complete search history.

(56) References Cited

U.S. PATENT DOCUMENTS

| | | | |
|---|---|---|---|
| 4,591,974 A | 5/1986 | Dornbush et al. | |
| 4,667,292 A | 5/1987 | Mohlenbrock et al. | |
| 4,839,806 A | 6/1989 | Goldfischer et al. | |
| 4,893,270 A | 1/1990 | Beck et al. | |
| 4,937,743 A | 6/1990 | Rassman et al. | |
| 4,962,475 A | 10/1990 | Hernandez et al. | |
| 5,072,383 A | 12/1991 | Brimm et al. | |
| 5,072,412 A | 12/1991 | Henderson, Jr. et al. | |
| 5,072,838 A | 12/1991 | Price, Jr. et al. | |
| 5,077,666 A | 12/1991 | Brimm et al. | |
| 5,088,981 A | 2/1992 | Howson et al. | |
| 5,101,476 A | 3/1992 | Kukla | |
| 5,253,362 A | 10/1993 | Nolan et al. | |
| 5,301,105 A | 4/1994 | Cummings, Jr. | |
| 5,319,543 A | 6/1994 | Wilhelm | |
| 5,325,478 A | 6/1994 | Shelton et al. | |
| 5,347,578 A | 9/1994 | Duxbury | |
| 5,361,202 A | 11/1994 | Doue | |
| 5,428,778 A | 6/1995 | Brookes | |
| 5,450,593 A | 9/1995 | Howell et al. | |

(Continued)

FOREIGN PATENT DOCUMENTS

WO WO-96/13790 A1 5/1996

(Continued)

OTHER PUBLICATIONS

Microsoft Press Computer Dictionary, Third Edition, 1997, pp. 416-417.*

(Continued)

*Primary Examiner* — Robert Morgan
*Assistant Examiner* — Michael Fuelling
(74) *Attorney, Agent, or Firm* — Boyle Fredrickson, S.C.

(57) ABSTRACT

A patient health record system uses knowledge bases to dynamically build visit templates and suggest content based on the user's profile and current patient information. The visit template is available to the health care provider using the system, and is presented within an easy-to-use graphical interface comprising a navigation pane for moving from one section of the template to another, and a visit information window that displays current visit information and allows the user to add and edit that information.

16 Claims, 5 Drawing Sheets

U.S. PATENT DOCUMENTS

| | | | |
|---|---|---|---|
| 5,471,382 A | 11/1995 | Tallman et al. | |
| 5,546,580 A | 8/1996 | Seliger et al. | |
| 5,557,515 A | 9/1996 | Abbruzzese et al. | |
| 5,574,828 A | 11/1996 | Hayward et al. | |
| 5,596,752 A | 1/1997 | Knudsen et al. | |
| 5,603,026 A | 2/1997 | Demers et al. | |
| 5,666,492 A | 9/1997 | Rhodes et al. | |
| 5,692,125 A | 11/1997 | Schloss et al. | |
| 5,724,584 A | 3/1998 | Peters et al. | |
| 5,740,800 A | 4/1998 | Hendrickson et al. | |
| 5,748,907 A | 5/1998 | Crane | |
| 5,751,958 A | 5/1998 | Zweben et al. | |
| 5,758,095 A | 5/1998 | Albaum et al. | |
| 5,760,704 A | 6/1998 | Barton et al. | |
| 5,772,585 A * | 6/1998 | Lavin et al. | 600/300 |
| 5,774,650 A | 6/1998 | Chapman et al. | |
| 5,778,346 A | 7/1998 | Frid-Nielsen et al. | |
| 5,781,442 A | 7/1998 | Engleson et al. | |
| 5,781,890 A | 7/1998 | Nematbakhsh et al. | |
| 5,802,253 A | 9/1998 | Gross et al. | |
| 5,823,948 A | 10/1998 | Ross, Jr. et al. | |
| 5,832,450 A | 11/1998 | Myers et al. | |
| 5,833,599 A | 11/1998 | Schrier et al. | |
| 5,838,313 A | 11/1998 | Hou et al. | |
| 5,842,976 A | 12/1998 | Williamson | |
| 5,845,253 A | 12/1998 | Rensimer et al. | |
| 5,845,255 A | 12/1998 | Mayaud | |
| 5,848,393 A | 12/1998 | Goodridge et al. | |
| 5,848,395 A | 12/1998 | Edgar et al. | |
| 5,850,221 A | 12/1998 | Macrae et al. | |
| 5,867,688 A | 2/1999 | Simmon et al. | |
| 5,867,821 A | 2/1999 | Ballantyne et al. | |
| 5,899,998 A | 5/1999 | McGauley et al. | |
| 5,907,829 A | 5/1999 | Kida | |
| 5,915,240 A | 6/1999 | Karpf | |
| 5,924,074 A | 7/1999 | Evans | |
| 5,929,851 A | 7/1999 | Donnelly | |
| 5,946,659 A | 8/1999 | Lancelot et al. | |
| 5,950,168 A * | 9/1999 | Simborg et al. | 705/3 |
| 5,960,406 A | 9/1999 | Rasansky et al. | |
| 5,974,389 A * | 10/1999 | Clark et al. | 705/3 |
| 5,983,210 A | 11/1999 | Imasaki et al. | |
| 5,987,498 A | 11/1999 | Athing et al. | |
| 5,997,476 A | 12/1999 | Brown | |
| 5,999,916 A | 12/1999 | Peters et al. | |
| 6,014,631 A | 1/2000 | Teagarden et al. | |
| 6,016,477 A | 1/2000 | Ehnebuske et al. | |
| 6,021,404 A | 2/2000 | Moukheibir | |
| 6,029,138 A | 2/2000 | Khorasani et al. | |
| 6,037,940 A | 3/2000 | Schroeder et al. | |
| 6,047,259 A | 4/2000 | Campbell et al. | |
| 6,063,026 A | 5/2000 | Schauss et al. | |
| 6,067,523 A | 5/2000 | Bair et al. | |
| 6,076,166 A * | 6/2000 | Moshfeghi et al. | 726/4 |
| 6,081,786 A | 6/2000 | Barry et al. | |
| 6,082,776 A | 7/2000 | Feinberg | |
| 6,139,494 A | 10/2000 | Cairnes | |
| 6,154,726 A | 11/2000 | Rensimer et al. | |
| 6,182,047 B1 | 1/2001 | Dirbas | |
| 6,185,689 B1 | 2/2001 | Todd, Sr. et al. | |
| 6,188,988 B1 | 2/2001 | Barry et al. | |
| 6,263,330 B1 | 7/2001 | Bessette | |
| 6,266,675 B1 * | 7/2001 | Evans et al. | 707/104.1 |
| 6,272,593 B1 | 8/2001 | Dujari | |
| 6,275,150 B1 | 8/2001 | Mandler et al. | |
| 6,279,033 B1 | 8/2001 | Selvarajan et al. | |
| 6,283,761 B1 | 9/2001 | Joao | |
| 6,289,368 B1 | 9/2001 | Dentler et al. | |
| 6,304,905 B1 | 10/2001 | Clark | |
| 6,317,719 B1 | 11/2001 | Schrier et al. | |
| 6,332,167 B1 | 12/2001 | Peters et al. | |
| 6,345,260 B1 | 2/2002 | Cummings, Jr. et al. | |
| 6,381,615 B2 | 4/2002 | Gaither et al. | |
| 6,389,454 B1 | 5/2002 | Ralston et al. | |
| 6,401,072 B1 | 6/2002 | Haudenschild et al. | |
| 6,415,275 B1 | 7/2002 | Zahn | |
| 6,516,324 B1 | 2/2003 | Jones et al. | |
| 6,522,875 B1 | 2/2003 | Dowling et al. | |
| 6,678,698 B2 | 1/2004 | Fredell et al. | |
| 6,725,200 B1 | 4/2004 | Rost | |
| 6,757,898 B1 | 6/2004 | Ilsen et al. | |
| 6,856,989 B1 | 2/2005 | Zhou et al. | |
| 2001/0016056 A1 | 8/2001 | Westphal et al. | |
| 2001/0016853 A1 | 8/2001 | Kucala | |
| 2001/0049610 A1 | 12/2001 | Hazumi | 705/3 |
| 2001/0051888 A1 | 12/2001 | Mayhak, Jr. et al. | |
| 2001/0056433 A1 | 12/2001 | Adelson et al. | |
| 2002/0001375 A1 | 1/2002 | Alcott et al. | |
| 2002/0001387 A1 | 1/2002 | Dillon | |
| 2002/0002473 A1 | 1/2002 | Schrier et al. | |
| 2002/0002535 A1 | 1/2002 | Kitchen et al. | |
| 2002/0007287 A1 | 1/2002 | Straube et al. | |
| 2002/0062229 A1 | 5/2002 | Alban et al. | |
| 2002/0188478 A1 | 12/2002 | Breeland et al. | |
| 2003/0061072 A1 | 3/2003 | Baker et al. | |
| 2003/0110059 A1 | 6/2003 | Janas, III et al. | |
| 2003/0200726 A1 | 10/2003 | Rast | |
| 2004/0034833 A1 * | 2/2004 | Kougiouris et al. | 715/513 |

FOREIGN PATENT DOCUMENTS

| | | |
|---|---|---|
| WO | WO-96/27163 A1 | 9/1996 |
| WO | WO-99/22330 A1 | 5/1999 |
| WO | WO-99/41682 A2 | 8/1999 |
| WO | WO-99/44162 A1 | 9/1999 |
| WO | WO-99/63473 | 12/1999 |
| WO | WO-00/28460 | 5/2000 |
| WO | WO-00/65522 A2 | 11/2000 |
| WO | WO-02/29664 A1 | 4/2002 |

OTHER PUBLICATIONS

Michihiro Hazumi and Toshio Kawamoto, "Development of Electronic Medical Record System," NEC Res. & Develop., vol. 41, pp. 102-105, Jan. 2000.

McDonald et al., The Regenstrief Medical Record System: a quarter century experience, International Journal of Medical Informatics, vol. 54, 1999, pp. 225-253.

"Sunrise Knowledge-Based Orders," Advanced Clinical Solutions, ECLIPSYS, www.eclipsys.com, Dec. 2002, 4 pages.

"Sunrise Clinical Manager," Advanced Clinical Solutions, ECLIPSYS, www.eclipsys.com, Dec. 2002, 4 pages.

"News & events," ECLIPSYS, www.eclipsys.com, Apr. 16, 2002, 3 pages.

"Horizon Clinicals," Mckesson Corporation, www.mckesson.com, 2003, 2 pages.

"Acute Care EMR—Solutions," Cerner Corporation, www.cerner.com, 2002-2003, 2 pages.

"Foundation," IDX Systems Corporation, www.idx.com, 1999-2004, 2 pages.

"Supporting the Work of Clinicians," IDX Systems Corporation, www.idx.com, 1999-2004, 1 page.

"Autonomy Update™", Product Brief, Autonomy Inc., www.autonomy.com, Mar. 2003, 2 pages.

"Brio.Portal", Sun Solutions Catalog, Sun Microsystems, www.sun.com, 1994-2002, 1 page.

"Portal-in-a-Box™," Product Brief, Autonomy Inc., www.automony.com, Apr. 2002, 6 pages.

"Actuate Software," Sun Solutions Catalog, Actuate Corporation & Sun Microsystems, www.sun.com, 2002, 24 pages.

"CDR-Web," Reliance Software Systems, Website, 2000, 1 page.

Marietti, "'O' Pioneers!," Healthcare Informatics, Website, May 1999, 9 pages.

Johnson, "Today's CDRs: The Elusive Complete Solution," Healthcare Informatics, (Website), Jul. 1997, 7 pages.

Andrew et al., "Computer-Based Patient Records—Venturing Off the Beaten Path: It's Time to Blaze New CPR Trails," Healthcare Informatics, (Website), May 1997, 17 pages.

"EMR Features," Care Is #1, 1999-2000, 1 page.

"Enterprise Systems Management," Cerner Corporation, www.cerner.com, Sep. 13, 2001, 5 pages.

"HealthMatics™ Office", Healthmatics Office, Website, 3 pages, (date unknown).

Clinicomp, Intl., Website, 1999-2000, 1 page.

"ExcelCare Windows", Website, 2 pages (date unknown).
"IC-Chart Information", Integreat, Website, 1 page, (date unknown).
"Managing mail messages with rules," Microsoft Outlook Help Manual, Website, Version 6, 5 pages Jun. 24, 2002.
Mercando, "Appointment Scheduling on Computer", PACE, vol. 20, Jul. 1997, pp. 1860-1862.
EncounterPRO, the Workflow Enabled CPR/EMR from JMJ Technologies, JMJ Technologies, Inc., www.jmjtech.com, Nov. 8, 2002, 6 pages.
"Expeditor Systems—The Patient Flow Systems Experts", Expeditor Systems, www.expeditor.com, 2001, 3 pages.
"Working with Patient Lists," EpicCare Inpatient Electronic Medical Record Jul. 2000 User's Guide, Epic Systems Corp., Section 10.5-10.6, 3 pages.
"Patient Lists," EpicCare Inpatient Electronic Medical Record Jul. 2000 User's Guide, Epic Systems Corp., Section 11.3-11.4, 3 pages.
"Oacis—Census Management," Dinmar (U.S.) Inc., www.oacis.com, 2002, 2 pages.
Grimson et al., "Interoperability Issues in Sharing Electronic Healthcare Records—the Synapses Approach," IEEE, 1997, pp. 180-185.
"Clinician Documentation with EMR," Clinicomp, Intl., www.clinicomp.com, 1999-2002, 1 page.
"Essentris™ CPOE", Clinicomp, Intl., www.clinicomp.com, 1999-2002, 2 pages.
"Essentris198 GDR," Clinicomp, Intl., www.clinicomp.com, 1999-2002, 2 pages.
"Intensivist Tools," Clinicomp, Intl., www.clinicomp.com, 1999-2002, 2 pages.
"CMRxp—Computerized Medical Records Powered by Experience!!," Electronic Medical Records (EMR)xp Experience, Chartcare, Inc., www.chartcare.com, Mar. 5, 2003, 2 pages.
"Dr-InBasket-Lab Results, Messaging and To-Do's," Chartcare, Inc., www.chartcare.com, Mar. 5, 2003, 3 pages.
"PatInfo-Patient Information Handouts," PatInfo-Patient Demographics Software, Chartcare, Inc., www.chartcare.com, Mar. 5, 2003, 2 pages.
"Recall-Patient Health Maintenance," Chartcare, Inc., www.chartcare.com, Mar. 5, 2003, 3 pages.
"LabTrack-Lab Ordering & Results Tracking," LabTrack-Lab Result Tracking Software, Chartcare, Inc., www.chartcare.com, Mar. 5, 2003, 3 pages.
"Rx-MedTrack-Prescription Writing/Medication Tracking," Rx-MedTrack-Prescription Writing Software, Chartcare, Inc., www.chartcare.com, Mar. 5, 2003, 2 pages.
"The Right Tools," Product Description, Integreat Inc., www.igreat.com, 2003, 1 page.
"IC-Chart Additional Modules," Integreat Inc., www.igreat.com, 2003, 2 pages.
"Services," Integreat Inc., www.igreat.com, 2003, 2 pages.
"HCS Order Communications Module," web.archive.org/hcsinteractant.com, 2000, pp. 1-3.
Ebidia et al., "Getting Data Out of the Electronic Patient Record: Critical Steps in Building a Data Warehouse for Decision Support," SIMS University Health Network, Dept. of Medicine, University of Toronto, Canada, Nov. 8, 1999, pp. 1-5.
"Patient1 Vista", PerSe Technologies, www.per-se.com/web.archive.org, 2000, 2 pages.
"Sunrise Clinical Manager", Eclipsys, Sunrise Clinical Overview, www.eclipsnet.com/web.archive.org, 1999, 1 page.
"American Medical Management Selects Tandem Computers as Systems Partner", PR Newswire, Feb. 20, 1997, 2 pages.
"Premier Members Select Cemer's Clinical Data Repository as a Result of Exclusive Endorsement", PR Newswire, Feb. 19, 1997, 2 pages.
"Physicians and Staff Go Online with Cemer's Clinical Data Repository and Orders Management", PR Newswire, Mar. 4, 1996, 2 pages.
"Patient1", PerSe Technologies, www.per-se.com/web.archive.org, 2000, 4 pages.
Plaisant et al., "An Information Architecture to Support the Visualization of Personal Histories," Information Processing & Management, vol. 34, No. 5, 1998, pp. 581-597.
Fabbretti et al., "Applying the Object Paradigm to a Centralized Database for a Cardiology Division," International Journal of Bio-Medical Computing, vol. 42, 1996, pp. 129-134.
Van De Velde, "Framework for a Clinical Information System," International Journal of Medical Informatics, vol. 57, 2000, pp. 57-72.
Egan et al., "Computers and Networks in Medical and Healthcare Systems," Comput. Biol. Med., vol. 23, No. 3, 1995, pp. 355-365.
IBM Research Disclosure, "Comprehensively managed user workspace," IBM, vol. 42, No. 421, May 1, 1999, 5 pages.
Bakman et al., Enhancing a WIMP based interference with Speech, Gaze tracking and Agents, 4 pages.
CPRS GUI, CPRS V 1.0 Clinician Guide, Apr. 26, 1999, 36 pages.
Kennedy Health, http://thunder/idxweb/idxps/patientservices.asp, 1999, 10 pages.
Leavitt et al., "Case Study: Giving Patients Online Access to Their Health Records," Presentation, Feb. 2000, 40 pages.
Miller, "Towards MedicaLogic.com, An Internet Strategy," MedicLogic, May 1999, 7 pages.
INHS/IRM-Inland Northwest Health Services, Mar. 2, 1999, 7 pages.
"Integrate About My Health Into Your Practice," MedicaLogic./Medscape, Inc., 2001, 5 pages.
Aboutmyhealth.net, website, Aug. 10, 1999, 27 pages.
Woody, "Why Your Medical File Belongs Online," PCWorld.com, Jul. 23, 1999, 2 pages.
"Integrate 98point6 Into Your Practice," MediaLogic, Inc., 2000, 16 pages.
Streveler, "eHealthcare is Reconnecting the Healthcare Industry," Mar. 20, 2000, 35 pages.
Leavitt, "MedicaLogic.com: @ the point of Car ," Presentation, 1999, 7 pages.
"Moving H althcare to the Web," The ChannelHealth, Dec. 9, 1999, 46 pages.
"IDX and ChannelHealth—Th Competition," May 15, 2000, 27 pag s.
Gray, "PING—The Personal Int m tworked Notary and Guardian," Children's Hospital Inf rmatics Program, http://www.chip. rg/research/ping.htm, Nov. 9, 2001, 17 pages.
Fletcher, "Current issues in confidentiality: Computerized information systems, medical records, and patient rights," ACM SIGCAS Computers and Society, vol. 16, Issue 2-3, Summer/Fall 1986, pp. 8-18.
Beckham, J. Daniel, "The engine of choice," Healthcare Forum Journal, vol. 39, No. 4, Jul./Aug. 1996.
Ho et al. Introducing variable-interval appointment scheduling rules in service systems, International Journal of Operations and Production Management, vol. 15, No. 6, 1995.

* cited by examiner

INTELLIGENT PATIENT VISIT INFORMATION MANAGEMENT AND NAVIGATION SYSTEM

CROSS-REFERENCE TO RELATED APPLICATIONS

This application claims priority to U.S. Provisional Patent Application Ser. No. 60/233,949, filed Sep. 20, 2000, the disclosure of which is hereby expressly incorporated herein by referenced.

FIELD OF THE INVENTION

The invention relates generally to information management systems for use within the healthcare enterprises, and more particularly, to an intelligent system and method for managing and navigating patient information.

BACKGROUND OF THE INVENTION

The provision of quality health care depends critically on timely and easy access to information that is most relevant to the patient's current condition. Computer-based clinical documentation systems have helped health care providers overcome many of the shortcomings of a paper-based system, including accessibility, portability, security and usability. However, as with any technological advance, the implementation of computer-based patient records has not only created new problems, but has also raised expectations about how health care information can be used in such a way that many of the known solutions and approaches are now seen as problematic.

The successful implementation of computer technology by health care providers demands that they acquire computer skills that many providers view as an infringement upon their primary purpose in seeing and treating patients. The demand for new skills and corresponding frustration is exacerbated by the increased expectations about the amount of patient information that should be recorded and available for use during any given patient encounter. The fact that a computer-based patient record presents a health care provider with a much larger set of potential information creates a corresponding imperative to both record and review more information while providing a patient's care. The problem is that eventually, the computer interface for accessing this wealth of information becomes nearly as cumbersome to deal with as a paper chart. Typing to enter information while clicking or scrolling through a myriad of windows, forms or screens can be as distracting and nearly as inefficient as flipping through pages of paper.

Existing computer-based record systems have partially resolved this problem by limiting the amount of manual typing and navigation required to access and record information for a given patient visit. A typical solution is to provide a summary of key data elements in a single window and to collapse access to the underlying data into a hierarchical navigation interface. The interface allows users to drill down to a specific data element by pointing and clicking within the interface, and to enter data by the same means. By presenting users with rapid access to information that is most relevant to their current patient visit, these solutions make it easier for health care providers to use and add to the information available within a computerized patient record. In order to ensure that these ease-of-use features remain flexible for use among diverse health care providers with even more diverse patient populations, it is even more desirable to embed these features as templates within the user interface. A template-based approach allows providers to choose from a number of different summary/navigation views and use the one that is most appropriate for the given circumstances.

However, this solution is ultimately unsatisfactory, because of the frequency with which health issues will arise that a template was not designed to address. The obvious attempts to resolve this difficulty also prove unsatisfactory. First, simply creating more templates means that the provider will face the problem of knowing the differences between each template in advance, and the choice may ultimately prove unsatisfactory anyway. For example, you could create a number of different variations of each standard template, but in order to use this set of variations efficiently you would have to be familiar with the specific differences between each template. And even if you choose what looks to be the right template at the start of a visit, you may uncover information in the course of that visit that is no longer easy to capture with the original template. Second, building more complexity into a smaller set of templates tends to defeat the purpose for having templates in the first place. The more complexity you add to a standard template, the more it looks like the complex system that the template is intended to simplify. Third, allowing a user to embed dictated notes to extend the usefulness of any given template undermines some of the advantages afforded by using a computerized record in the first place. Dictated notes must be transcribed if they are to be viewable online, and the elimination of transcription costs is one of the major benefits associated with implementing a computerized health record system. Even if you manage to successfully automate the transcription process, you lose the benefits associated with storing visit information as structured data. Dictation blocks of text, because they are unstructured (i.e., are filed in the database as free text rather than as discrete data items such as diagnosis codes), are unavailable for use in decision support, data mining and reporting.

So even with the above-listed improvements, the tension between ease-of-use and flexibility for recording patient encounter information persists within existing solutions to providing a computerized patient record. The objective of the present invention is to provide a computerized patient record system that takes full advantage of an easy-to-use navigation interface and summary view but which does so without sacrificing the flexibility and power associated with a robust database of information.

DETAILED DESCRIPTION OF THE PREFERRED EMBODIMENTS

In accordance with an embodiment of the invention, a patient health record system uses knowledge bases to dynamically build visit templates and suggest content based on the user's profile and current patient information. The visit template is available to the health care provider using the system, and is presented within an easy-to-use graphical interface comprising a navigation pane for moving from one section of the template to another, and a visit information window that displays current visit information and allows the user to add and edit that information.

Figure 1:
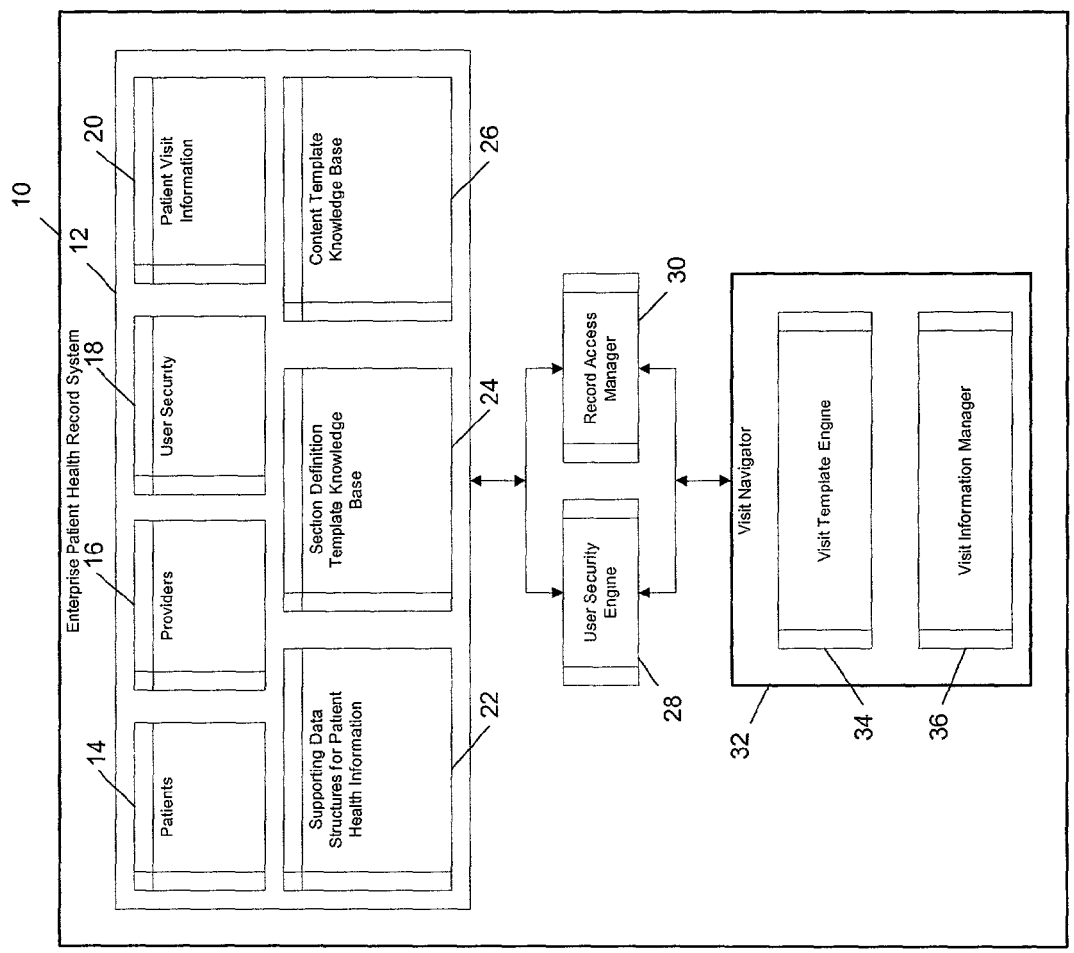
FIG. 1 is a block diagram illustrating a patient health record system in accordance with a preferred embodiment of the present invention.

Referring to FIG. 1, an enterprise patient health record system 10 includes a number of data elements 12 for supporting the patient information needs of the healthcare enterprise. As shown in FIG. 1, the system 10 includes a patients element 14, a providers element 16 and a user security element 18. These elements, for example, provide to the system 10 respective data services. For example, the patient element 14 includes a data structure for organizing and storing patient information and may incorporate processing and communication capability to allow the element to interface with the other elements of system 10 for receiving, organizing and storing patient information and for retrieving and delivering patient information. Of course the processing and communication capability may be centralized within the system 10, in which case the respective element would include just the appropriate data structure for organizing and retaining data. The system 10 further includes supporting data structure element 22 to fully support patient health records.

The system 10 also includes a patient visit information element 20. The patient visit information element 20 contains the information types that are used to dynamically build templates as well as to provide content suggestion. As will be described in more detail below, the visit template for the patient visit contains sections for displaying, recording and updating different types of visit information. These types of information include, but are not limited to, patient vital signs, medications, allergies, nursing notes, charting notes, progress notes, problem list, diagnoses, orders, patient instructions, follow up, level of service and any other information that may be relevant to the patient's visit. This information is stored in the system 10 for the particular patient along with other information necessary for maintaining the patient health records.

Further included with the data elements 12 are a section definition template knowledge base 24 and a content template knowledge base 26. The section definition template knowledge base 24 contains visit information types that are grouped into section definition templates. These templates are linked to encounter types, e.g., "office visit." The content template knowledge base 26 contains individual content selections that are grouped into content templates. These templates are linked to locator data that are documented as part of the visit, such as "chief complaint—back pain."

The data elements 12 are linked within the system 10 to the visit navigator tool 32 via a user security engine 28 and a record access manager 30. The user security engine 28 provides view and edit access security to limit user access to patient information in accordance with user security information, such as security profile, role, etc. The user security information is maintained within the user security element 18. The record access manager 30 locks patient records in response to user actions. The entire patient record is not locked, such that information unrelated to the visit encounter becomes unavailable system wide. Instead, only the portion relevant to the user's actions is locked. This provides for higher availability of patient information throughout the system.

The tool 32 includes a visit template engine 34 and a visit information manager 36. The visit template engine 34 determines sections (visit information types) to be included in the visit template based on the user profile, encounter type, and the section definition template knowledge base 24. The visit template engine 34 uses the current patient information as well as the content template knowledge base to add suggested content to the visit template. The user is permitted to select suggested content with point-and-click or similar actions. In addition, the tool 32 can be configured to allow changes and updates to visit templates in response to changes to the visit information. The visit information manager 36 processes the user's input and updates the display of the visit information.

Figure 2:
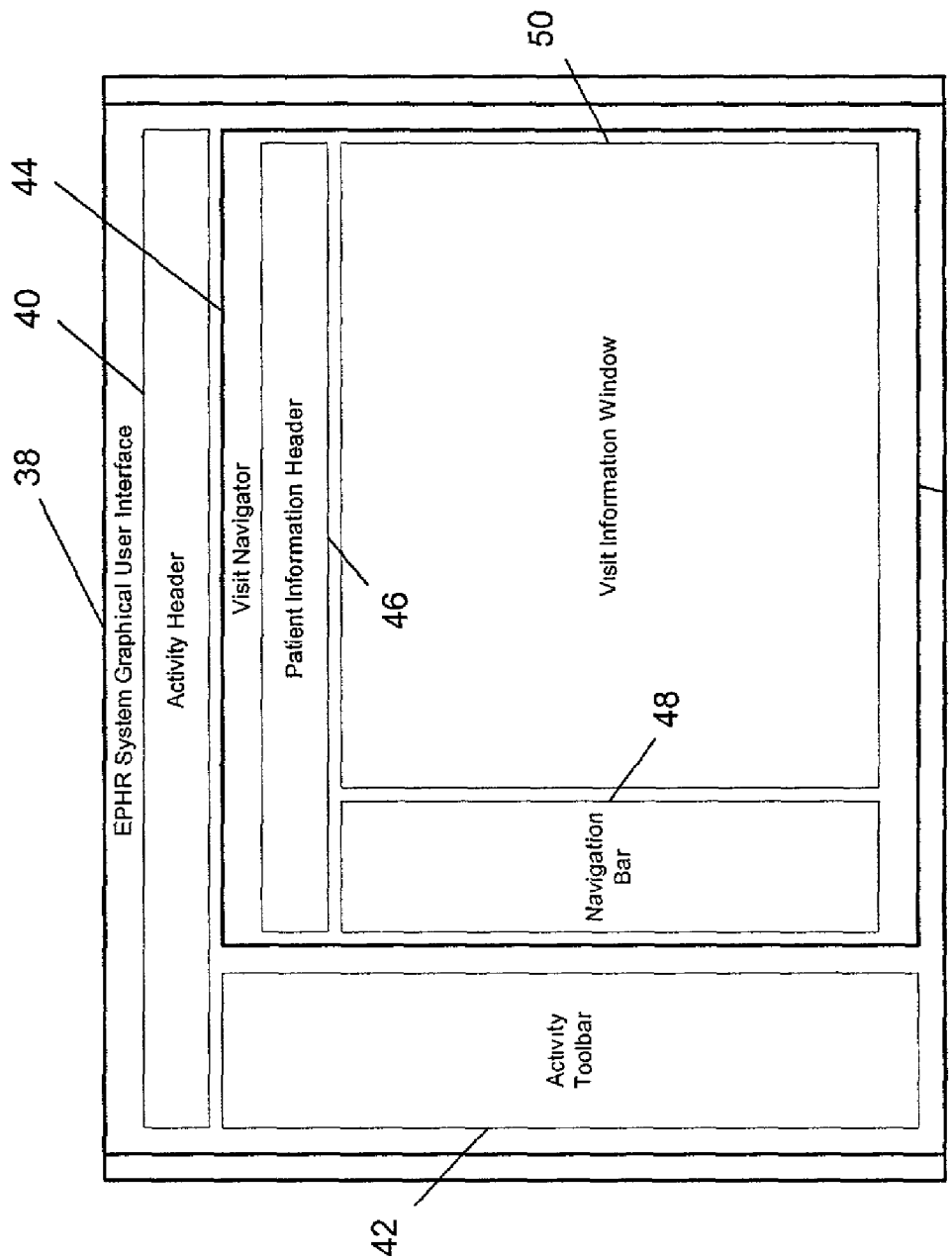
FIG. 2 is a block diagram illustration of a graphic user interface of the patient health record system illustrated in FIG. 1.

The tool 32 drives a graphic user interface (GUI) 38 shown in FIG. 2. The GUI 38 may have a web browser or other suitable appearance, and includes an activity header 40, an activity toolbar 42 and a template section 44. The activity header may provide patient information, such as patient name, sex, age, insurance and other demographic information. The activity toolbar 42 contains point-and-click activity selections, which allows the user to activate the tool 32, obtain patient information from the system, place orders, complete the encounter, etc.

Within the template section 44, there is a patient information header 46, a navigation bar 48 and a visit information window 50. The patient information header 46 provides general patient information for the current patient. For example, the current patient's known allergies and vital signs may be displayed. The information within the header 46 can be configured to display different information based on the user profile, the encounter type, etc. The navigation bar 48 permits the user to jump to corresponding sections of the visit information within the visit information window 50 using point-and-click or similar action. Within the visit information window 50, the user is able to select suggested content with point-and-click or similar action. The user can also scroll through information and select any section of information to expand it for editing.

In use, when the user creates a new patient visit record or opens an existing record, the tool 32 dynamically builds the visit template within the visit information window and suggests content using the visit template engine 34. The engine 34 first determines what sections of visit information (as described above) are appropriate for the user and the encounter type. Section definitions for visit templates are maintained in a section definition template knowledge base 24. The section definition template for an office visit may define all of the sections listed above for the visit template, while the template for an immunization administration encounter would define fewer sections.

The system 10 also checks the user's security profile for a specified section definition template that corresponds with the visit's assigned encounter type. If there are no templates defined in the user's profile, the visit template engine 34 uses a default section definition template. The system displays the sections that compose the selected visit template in the navigation pane 48 and the visit information window 50.

Within each section of visit information, the engine 34 may display suggested content that is appropriate for the current user, visit and/or patient health status. The visit template engine 34 retrieves suggested content from the content template knowledge base 26, adding individual content selections to corresponding sections within the visit template (for example, "Common migraine" to the Diagnosis section).

The engine 34 also suggests content for any section based on a variety of patient, user and visit information. This information—chief complaint, visit diagnoses, department specialties, etc., is linked to content templates as locator data. When the data documented during a visit matches the locator data assigned to a content template, the engine 34 selects that content template. For example, if a content template has a chief complaint locator of "physical exam," when the user documents "physical exam" as the visit's chief complaint, the content template is incorporated into the visit template.

The engine 34 may operate in a substantially more intelligent manner than simply suggesting templates based on one or more pieces of patient information taken from the current encounter. The engine 34 is designed to intelligently suggest content for the template based upon all available information known about the patient retained in the system 10, to develop content for the template presented to the caregiver. Thus, the engine 34, working from the content template knowledge base 26 and using all of the available patient information, such as, current medications, lab results, lab trends, problem list, etc., builds the template during the visit.

The system 10 can also dynamically update content suggestions as visit information is changed or added within the visit information window, thereby constantly responding to the user's input. For example, after a doctor enters a visit diagnosis the tool 32 may dynamically suggest patient instructions, medications, or follow-up actions appropriate to that diagnosis. The doctor can then either follow the rule-based suggestions with a simple point-and-click action or similar selection mechanism, or can alternatively select other actions by using the pop up editing window for the given content type.

Suggested content can include such things as individual diagnosis and procedure codes, medications, and blocks of text specifically geared towards the current patient through automatic links to patient record information (vitals, lab results, etc.). Additional suggested content may include best practices guidelines, which may help prevent errors by preventing errors of omission. The user can use suggested content by selecting the appropriate command in the visit information window 50.

In addition to links to patient-specific information, the text blocks described above can contain user-defined selection lists that allow the user to quickly tailor the text to a specific patient visit by selecting the proper elements within the selection list (for example, "in mild distress" from a "General Appearance" selection list). Within the system 10 the selection lists can be configured as structured data (i.e., filed in the database as discrete data items) for reporting and decision support purposes. In addition to using suggested content, the user can also add his or her own content by either typing directly in text fields or by typing entries or using drop down lists for discrete data items.

Within the visit information window 50, all sections are displayed as read-only text until a user with editing security opens a section for editing by selecting the appropriate command. The section then expands from view-only to editing mode and the data elements contained therein are locked from editing by any other user by the record access manager 30. This inline expansion not only makes it easier to scan and read the visit information because it is all listed in an easy-to-scroll window, but it also makes it easy for multiple users to view and edit information in the patient visit without data conflicts, because a section is not locked until a user activates it for editing. With this data-locking scheme a nurse could be documenting the administration of an immunization while the physician updates progress notes for the visit or documents the visit diagnoses or level of service.

The system 10, by combining an easy to use navigation and information interface with knowledge base-driven templates, represents a solution that is both easier to use and more flexible than existing systems. Users of this system can harvest the full potential of a computerized patient record without need of extensive data-entry and computer expertise.

Figure 3:
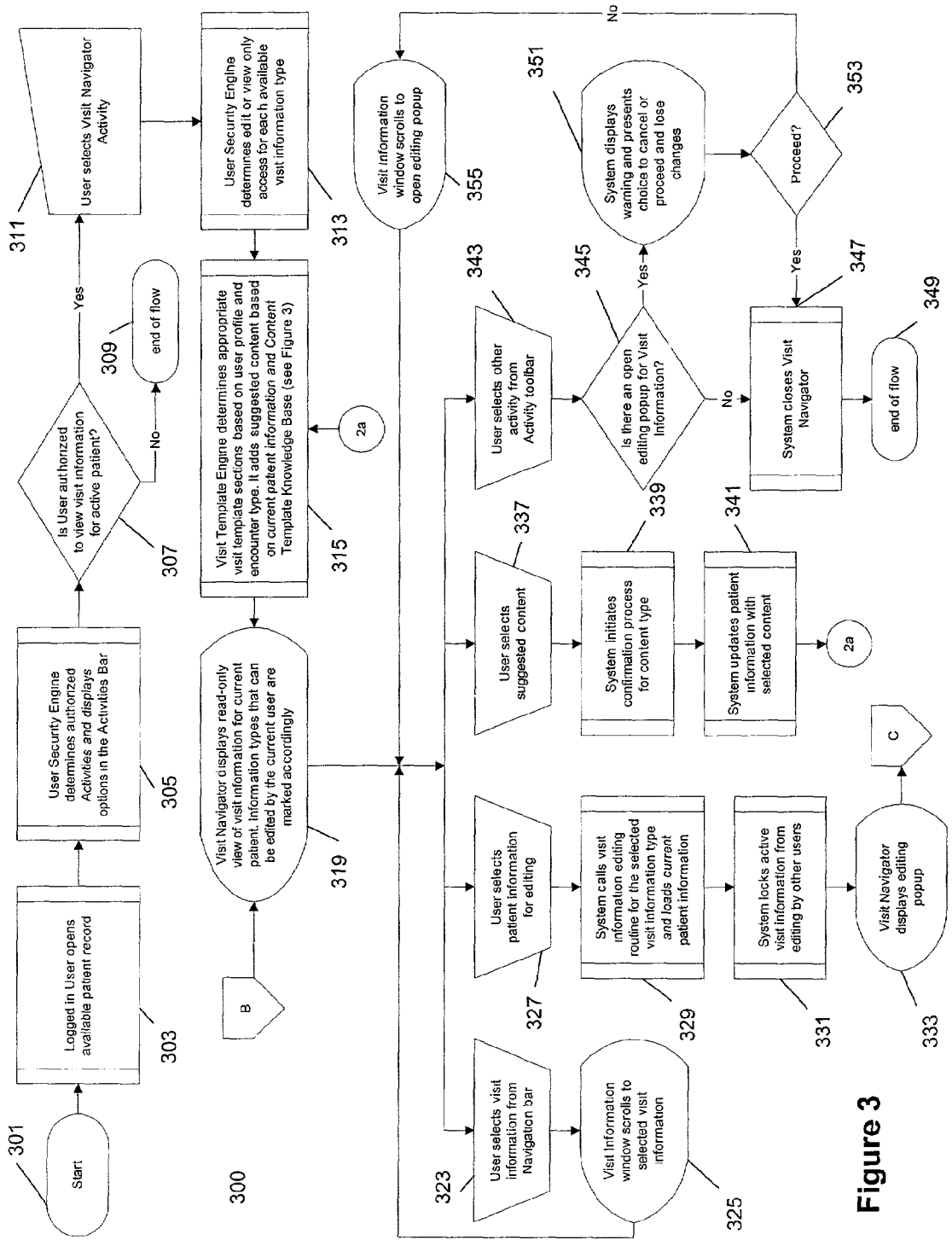
FIG. 3 is a flowchart representing the general operation of a system in accordance with a preferred embodiment of the invention.

Referring now to FIG. 3, the user workflow 300 is described in additional detail. Starting at 301, a logged in user opens an available patient record, 303. Upon doing so, the user security engine 28 determines authorized activities for the user and displays options in the activity bar 42 of the GUI 38, 305. Based on the user security profile, if the user is not authorized to view the visit information for the active patient, 307, the workflow ends, 309. Otherwise, to activate the visit navigation tool 32, the user selects the visit navigation activity from the activity toolbar 42.

Again, based on the user's security profile, the user security engine 28 determines whether edit or view only access is available to the user for each type of visit information, 313. At 315, the tool 32 determines appropriate visit template sections based on the user profile and encounter type using the section definition template knowledge base 24, 315, and adds suggested content based on current patient information using the content template knowledge base 26, 315. The tool 32 then displays the read-only view of the visit information for the current patient in the visit information window 50, and marks information types that can be edited by the current user, 319.

From within the visit information window 50, the user may perform a number of different tasks including: selecting visit information from the navigation bar 48, 323; selecting patient information to edit from within the visit information window 50, 327; selecting suggested content from within the visit information window 50, 337; and selecting another activity from the activity toolbar 42, 343. When the user selects visit information from the navigation bar 48, 323 the visit information window 50 scrolls to the selected visit information 325. Selecting patient information to edit 327 causes the tool 32 to call a visit information editing routine for the selected visit information type, and loads the patient information to be edited, 329. The record access manager 30 locks the active visit information within the system 10, 331, so that others may not edit it. The tool 32 then displays an editing popup in the visit information window 50. Selecting suggested content 337 causes the tool 32 to perform a confirmation process for the content type, 339. The confirmation process, which may occur before the user is presented with a list of choices of selected content, verifies that the suggested content is appropriate for the age, gender, etc. of the patient to ensure the caregiver is only presented with a valid list of choices. The tool 32 updates the patient information with the selected content, 341.

Selecting another activity from the activity toolbar 42, 343 causes a number of actions. First, if there is an open editing popup for visit information, 345, the tool 32 displays a warning and presents choices to cancel or proceed and lose changes to any edited information, 351. By selecting not to proceed, 353, the visit information window 50 scrolls to the open editing popup, 355. If there are no active editing popups, 345, or if the user elects to proceed, 353, the tool 32 closes, 347 and the workflow is ended 349.

Figure 4:
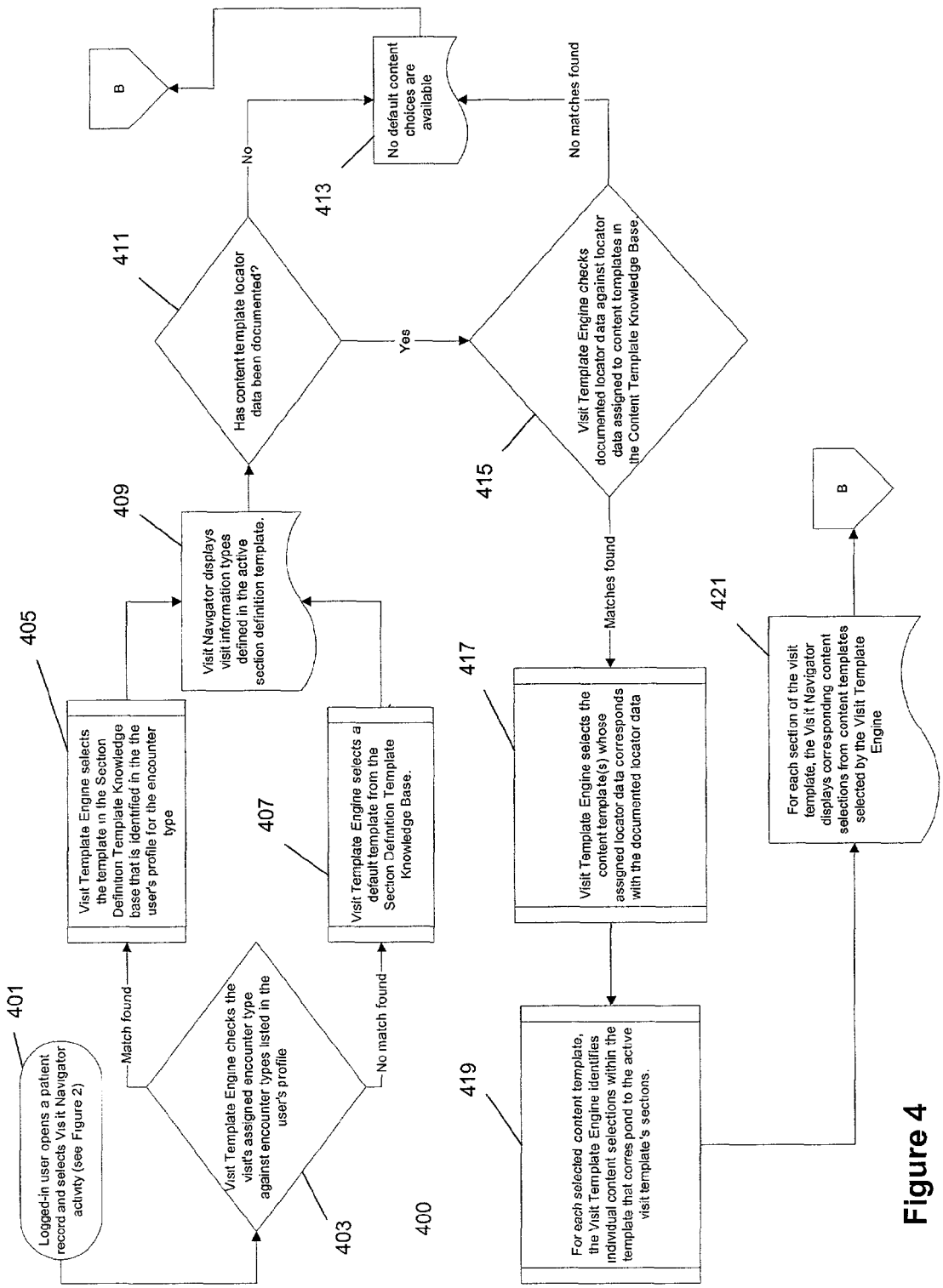
FIG. 4 is a flowchart representing a visit template engine in accordance with a preferred embodiment of the invention.

Referring now to FIG. 4, the workflow 400 associated with the visit template engine 34 is discussed in greater detail. When a logged-in user opens a patient record and selects the visit navigation tool 32 activity, 401, the visit template engine 34 checks an encounter type assigned to the visit against encounter types listed in the user's profile, 403. If there is a match found, the engine 34 selects the template from the section definition template knowledge base 24 that is identified in the user's profile for that encounter type, 405. Otherwise, the engine 34 selects a default template from the section definition template knowledge base 24, 407. The tool 32 then displays in the visit information window 50, the visit information types defined in the active, i.e., selected, section definition template, 409.

A check is made to determine if content template locator data has been documented, 411. If not, no default content choices are available, 413, resulting in no matches being found. If content template locator data is documented, the engine 34 checks documented locator data against locator data assigned to content templates in the content template knowledge base 26, 415. The engine 34 then selects the content template(s) whose assigned locator data corresponds to the documented locator data, 417, and for each selected content template, the engine 34 identifies individual content selections within the template that correspond to the active sections of the selected visit template, 419. For each section of the visit template, the tool 32 displays corresponding content selections from the content templates selected by the engine 34, 421.

Figure 5:
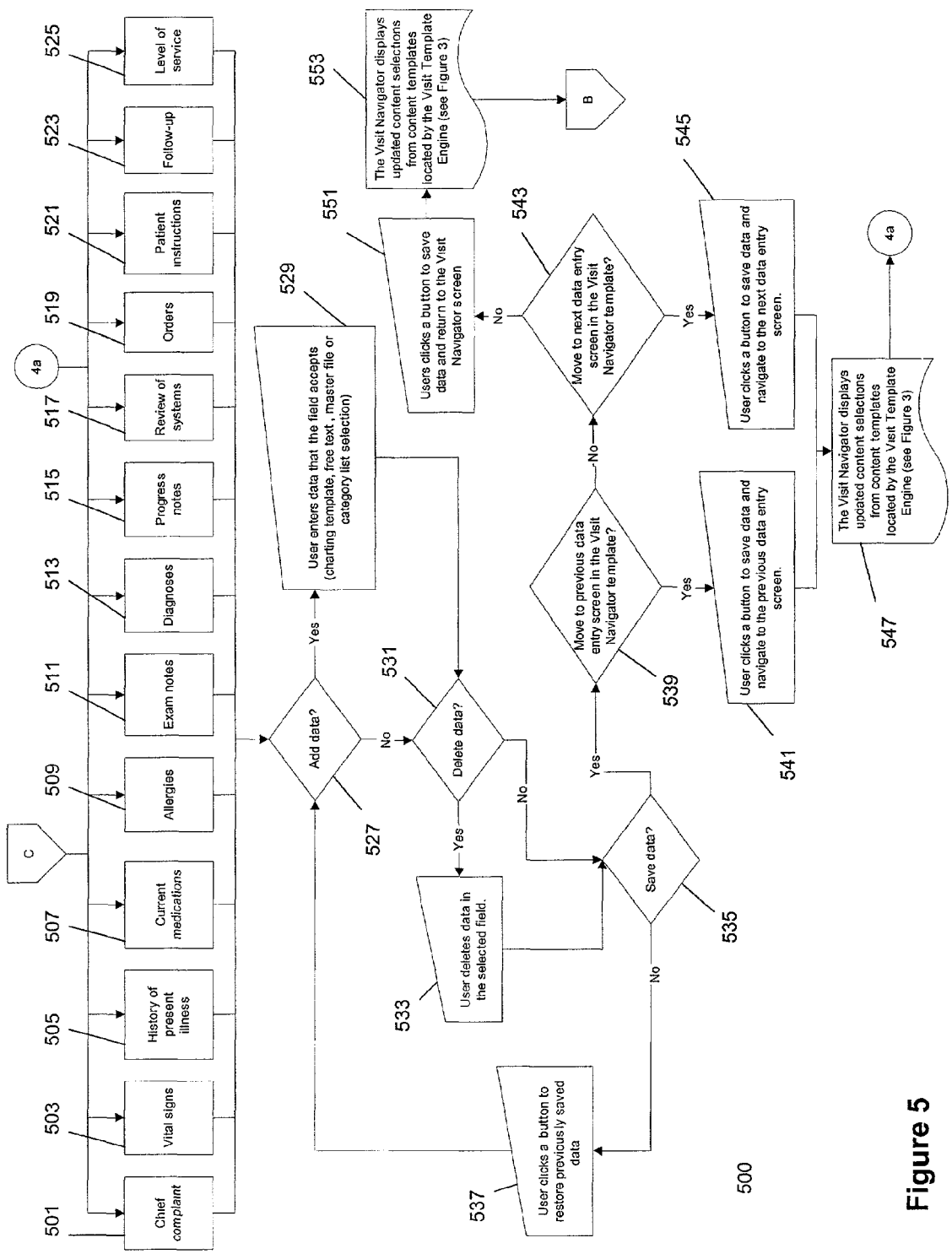
FIG. 5 is a flowchart representing a process for editing visit information.

FIG. 5 illustrates the workflow 500 for editing visit information. When a user selects patient information for editing (327 of FIG. 3), the result is an editing popup being displayed in the visit information window (333 of FIG. 3), which starts the editing workflow, 500. Exemplary types of visit information that may be edited are: chief complaint, 501; vital signs, 503; history of present illness, 505; current medications, 507; allergies, 509; exam notes, 511; diagnoses, 513; progress notes, 515; review of systems, 517; orders, 519; patient instructions, 521; follow-up, 523; and level of service, 525. If data is to be added, 527, the user enters the data based upon the fields for the data, e.g., charting template, free text, master file, or category list selection, 529. Standardized words and phrases, and methods to predict words and phrases to be entered, may be used to facilitate and simplify the data entry. Data may also be deleted, 531, by deleting data from the selected field, 533. After either adding or deleting data, the user is offered the opportunity to save the edited data, 535. If the user decides not to save the edited data, 535, the user clicks a button to restore the previously saved data 537, and the editing popup remains open. If the user elects to save the edited data, 535, the user may elect to move to the previous data entry screen in the visit template, 539. Doing so causes the data to be saved and the tool 32 to navigate to the previous data entry screen, 541. The tool 32 then displays the updated content selections from the content templates located by the engine 34, 547. If the user elects not to move to the previous data entry screen, 539, the user may elect to move to the next data entry screen, 543. Doing so causes the edited data to be saved, and the tool 32 to navigate to the next data entry screen, 545. The tool 32 then displays the updated content selections from the content templates located by the engine 34, 547. The user may elect not to edit the next data entry 543, ending data editing. Doing so causes the edited data to be saved, 551 and the tool 32 to display the updated content selections from the content templates located by the engine 34, 553 and returns to the workflow 300.

The invention has been described in terms of several embodiments, including a number of features and functions. Not all features and functions are required for every embodiment of the invention, and in this manner the invention provides a flexible system by which a user may manage and navigate patient visit information. The features discussed herein are intended to be illustrative of those features that may be implemented; however, such features should not be considered exhaustive of all possible features that may be implemented in a system configured in accordance with the embodiments of the invention.

We claim:

1. A system for assisting healthcare providers in entering patient visit data in a database comprising:
    a database holding patient visit data providing clinical information about a patient visit to a healthcare provider and at least one of other patient information and healthcare provider information;
    a set of section-definition templates defining at least one section for an entry of patient visit data by the healthcare provider;
    a visit template engine communicating with the set of section-definition templates and operating to:
        (1) automatically select section-definition templates from the set of section-definition templates to create a visit template having sections;
        (2) monitor entry of patient visit information by the healthcare provider into the sections of the visit template; and
        (3) automatically modify the selection of the section templates contemporaneously with the entry of patient visit information into the sections to modify the sections forming the visit template in response to patient visit information entered into sections of the visit template by a user to provide different sections in the visit template for the entry of patient visit data.

2. The system for assisting healthcare providers of claim 1 wherein the visit template engine further operates to:
    automatically select at least one content template proposing patient visit data to be entered into a section of the visit template; and
    wherein each content template is linked to locator data and wherein the selected content template is automatically selected based on a match between the locator data and the patient visit data entered into another section of the visit template.

3. The system of claim 2 wherein the selected content template is automatically selected based on a match between the locator data and other clinical patient data in the database related to the patient visit data.

4. The system of claim 1 wherein the section-definition templates are each linked to an encounter type describing a type of visit and wherein the selected section-definition templates are automatically selected based on an encounter type.

5. The system of claim 4 wherein the encounter type is selected from the group consisting of office visits and immunization administrations.

6. The system of claim 1 wherein the sections of the section-definition templates are selected from the group consisting of: patient vital signs, medications, allergies, nursing notes, charting notes, progress notes, problem list, diagnoses, orders, patient instructions, follow up, and level of service.

7. The system of claim 1 wherein the section-definition templates are further selected according to a user profile containing information about a health care provider.

8. The system of claim 1 wherein multiple users may simultaneously enter patient visit data into different sections of the visit template and only one user may enter data into a given section of the visit template at one time.

9. A computer-implemented method for assisting healthcare providers in entering patient visit data in a database comprising the steps of:
    (1) automatically selecting section-definition templates from a set of section-definition templates stored in a computer database to create a visit template having sections, each section-definition template defining at least one section for an entry of patient visit data;

(2) monitoring entry of patient visit information into the sections of the visit template by a user using a computer-implemented graphical user interface;

(3) automatically modifying the selection of the section templates comprising the visit template during the entry of patient visit information into the sections by the user in response to patient visit information entered into sections of the visit template by the user, the modification changing sections in the visit template that receive patient visit data; and (4) enrolling the patient visit information from the visit template into a computer database holding patient visit data.

10. The method of claim 9 further including the steps of:

automatically selecting at least one content template proposing patient visit data to be entered into the sections of the visit template wherein each content template is linked to locator data; and wherein the content template is automatically selected based on a match between the locator data and the patient visit data entered into another section of the visit template.

11. The method of claim 10 wherein the selected content template is automatically selected based on a match between the locator data and other clinical patient data in the database related to the patient visit data.

12. The method of claim 9 wherein the section-definition templates are each linked to an encounter type describing a type of visit and wherein the selected section-definition templates are automatically selected based on an encounter type.

13. The method of claim 12 wherein the encounter type is selected from the group consisting of office visits and immunization administrations.

14. The method of claim 9 wherein the sections of the section-definition templates are selected from the group consisting of: patient vital signs, medications, allergies, nursing notes, charting notes, progress notes, review of systems, problem list, diagnoses, orders, patient instructions, follow up, and level of service.

15. The method of claim 9 wherein the section-definition templates are further selected according to a user profile containing information about a health care provider.

16. The method of claim 9 including the step of allowing multiple users to simultaneously enter patient visit data into different sections of the visit template while prohibiting more than one user at a time from entering data into a given section of the visit template.

* * * * *